United States Patent
Tanaka et al.

(10) Patent No.: US 12,090,223 B2
(45) Date of Patent: Sep. 17, 2024

(54) METHOD OF MANUFACTURING COSMETIC COMPOSITIONS COMPRISING SUCROSE ESTERS AND SOLVENTS

(71) Applicant: The Procter & Gamble Company, Cincinnati, OH (US)

(72) Inventors: Shuhei Tanaka, Singapore (SG); Akiko Tada, Taokyo (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/549,970

(22) Filed: Dec. 14, 2021

(65) Prior Publication Data
US 2022/0183946 A1    Jun. 16, 2022

Related U.S. Application Data

(60) Provisional application No. 63/124,870, filed on Dec. 14, 2020.

(51) Int. Cl.
*A61K 8/60* (2006.01)
*A61K 8/36* (2006.01)
*A61Q 19/00* (2006.01)

(52) U.S. Cl.
CPC .............. *A61K 8/60* (2013.01); *A61K 8/361* (2013.01); *A61Q 19/00* (2013.01); *A61K 2800/805* (2013.01)

(58) Field of Classification Search
CPC .... A61K 8/60; A61K 8/361; A61K 2800/805; A61K 2800/49; A61K 8/34; A61K 8/345; A61K 8/375; A61K 8/06; A61Q 19/00; A61Q 19/02; A61Q 19/08
See application file for complete search history.

(56) References Cited

U.S. PATENT DOCUMENTS

| | | | |
|---|---|---|---|
| 5,534,554 A * | 7/1996 | Katz | A61P 31/02 514/939 |
| 5,635,165 A * | 6/1997 | Panitch | A61K 8/26 424/68 |
| 5,776,475 A * | 7/1998 | Kilpatrick-Liverman | A61K 8/042 424/401 |
| 6,548,074 B1 | 4/2003 | Mohammadi | |
| 8,206,721 B2 | 6/2012 | Stutz et al. | |
| 9,192,558 B2 | 11/2015 | Chen et al. | |
| 9,676,696 B2 | 6/2017 | Hakozaki | |
| 9,949,917 B2 * | 4/2018 | Moussou | A61Q 19/02 |
| 2003/0207817 A1 | 11/2003 | Ide | |
| 2005/0220726 A1 * | 10/2005 | Pauly | A61Q 19/02 424/70.13 |
| 2006/0018860 A1 | 1/2006 | Chen et al. | |
| 2011/0086115 A1 | 4/2011 | Mercier et al. | |
| 2014/0370098 A1 | 12/2014 | Terrisse et al. | |
| 2015/0352017 A1 | 12/2015 | Foley | |
| 2016/0206590 A1 | 7/2016 | Nadau-fourcade | |
| 2022/0183947 A1 | 6/2022 | Tanaka et al. | |

FOREIGN PATENT DOCUMENTS

| | | |
|---|---|---|
| CN | 107308018 A | 11/2017 |
| CN | 108619033 A | 10/2018 |
| CN | 109010102 A | 12/2018 |
| CN | 109875938 A | 6/2019 |
| CN | 110522686 A | 12/2019 |
| DE | 102007022448 A1 | 3/2008 |
| DE | 102011110749 A1 | 2/2013 |
| EP | 3078365 A1 | 10/2016 |
| EP | 3173064 A1 | 5/2017 |
| JP | H04117314 A | 4/1992 |
| JP | S63264512 A | 11/1998 |
| JP | 2002322027 A | 11/2002 |
| JP | 2002322028 A | 11/2002 |
| JP | 2003040724 A | 2/2003 |
| JP | 2004010598 A | 1/2004 |
| JP | 2004238354 A | 8/2004 |
| JP | 2004238355 A | 8/2004 |
| JP | 2005082553 A | 3/2005 |
| JP | 3754945 B2 | 12/2005 |

(Continued)

OTHER PUBLICATIONS

Nelen et al., 7 Sucrose Esters, Emulsifiers in Food Technology, John Wiley & Sons, second edition, 2015, 1-34 (Year: 2015).*
Section XIV Trade-Named Raw Materials, Cosmetic and Toiletry Formulations, vol. 3, vol. 3, 1995, 430-433 (Year: 1995).*
Safety and Ssessment of Sccharide Esters as Used in Cosmetics, Cosmetic Ingredient Review, Jun. 23, 2016, 1-65 (Year: 2016).*
Nelen, Ch 7 Sucrose Esters, Emulsifiers in Food Technology Second Edition (Year: 2015).*

(Continued)

*Primary Examiner* — David J Blanchard
*Assistant Examiner* — Edwin Coleman Mitchell
(74) *Attorney, Agent, or Firm* — Alexandra S. Anoff

(57) ABSTRACT

A method of manufacturing a cosmetic composition by preparing a mixture that includes a sucrose esters and one or more solvents. The sucrose ester can have a fatty acid portion having from about 12 to about 24 carbon atoms and the sucrose esters can be selected from the group consisting of mono-ester, di-ester, tri-ester, tetra-ester, and mixtures thereof. The one or more solvents can have Hildebrand Solubility Parameter of from about 23 to about $31.5 (J/cm^3)^{1/2}$ and Polar component of Hansen Solubility Parameter of from about 4.5 to about 10.5 $(J/cm^3)^{1/2}$. The sucrose ester can be dissolved in the cosmetic compositions, even when the sucrose ester is contained at higher levels in the compositions and/or even when the sucrose esters are contained in an aqueous phase of the cosmetic composition.

15 Claims, No Drawings

(56) References Cited

FOREIGN PATENT DOCUMENTS

| | | | |
|---|---|---|---|
| JP | 2006282588 A | 10/2006 | |
| JP | 3878095 B2 | 11/2006 | |
| JP | 2006312653 A | 11/2006 | |
| JP | 2006327965 A | 12/2006 | |
| JP | 3910094 B2 | 2/2007 | |
| JP | 2007022923 A | 2/2007 | |
| JP | 2011001289 A | 1/2011 | |
| JP | 5799328 B2 | 9/2015 | |
| JP | 2015193618 A | 11/2015 | |
| JP | 6097901 B2 | 3/2017 | |
| KR | 20180106106 A | 10/2018 | |
| KR | 20180106778 A | 10/2018 | |
| WO | 2006115190 A1 | 11/2006 | |
| WO | 2009124971 A2 | 10/2009 | |
| WO | WO-2011119228 A1 * | 9/2011 | ............... A23L 2/52 |
| WO | 2013023641 A2 | 2/2013 | |
| WO | 2013049580 A2 | 4/2013 | |
| WO | 2013125282 A1 | 8/2013 | |
| WO | 2014076136 A1 | 5/2014 | |
| WO | 2015167535 A1 | 11/2015 | |

OTHER PUBLICATIONS

Valentine, Bustle, The 5 Best Essential Oils for Deodorant, https://www.bustle.com/p/the-5-best-essential-oils-for-deodorant-18697144, published Sep. 13, 2019 (Year: 2019).*
Lesielle, INCI: Pentylene glycol, https://www.lesielle.com/US/pentylene-glycol-in-skincare-what-is-inci-1295 (Year: 2023).*
"Eye Cream", http://www.gnpd.com, Jul. 2019, pp. 1-7.
AA01442M PCT Search Report and Written Opinion for PCT/US2021/062319 dated Mar. 25, 2022, 30 pages.
All Office Actions; U.S. Appl. No. 17/549,975, filed Dec. 14, 2021.
Draelos, "Active agents in common skin care products", Plast Reconstr Surg, 125(2), Feb. 2010, pp. 719-724.

* cited by examiner

METHOD OF MANUFACTURING COSMETIC COMPOSITIONS COMPRISING SUCROSE ESTERS AND SOLVENTS

FIELD OF THE INVENTION

The present invention is directed to a method of manufacturing a cosmetic composition comprising a step of preparing a mixture of: (a) one or more esters of sucrose and fatty acids, wherein the fatty acids are selected from those having from about 12 to about 24 carbon atoms, and wherein the sucrose esters are selected from the group consisting of mono-ester, di-ester, tri-ester, tetra-ester, and mixtures thereof; and (b) one or more solvents selected from those having Hildebrand Solubility Parameter of from about 23 to about $31.5 (J/cm^3)^{1/2}$ and Polar component of Hansen Solubility Parameter of from about 4.5 to about 10.5 $(J/cm^3)^{1/2}$. By the method of manufacturing the cosmetic composition of the present invention, the sucrose esters can be dissolved in the cosmetic compositions, even when the sucrose esters are contained at higher levels in the compositions and/or even when the sucrose esters are contained in an aqueous phase of the cosmetic composition.

BACKGROUND OF THE INVENTION

Mammalian keratinous tissue, particularly human skin, is subjected to a variety of insults by both extrinsic and intrinsic factors. Such extrinsic factors include ultraviolet radiation, environmental pollution, wind, heat, infrared radiation, low humidity, harsh surfactants, abrasives, etc. Intrinsic factors, on the other hand, include chronological aging and other biochemical changes from within the skin. Whether extrinsic or intrinsic, these factors result in visible signs of skin damage. Typical skin damage in aging or damaged skin include fine lines, wrinkling, hyperpigmentation, sallowness, sagging, dark under-eye circles, puffy eyes, enlarged pores, diminished rate of turnover, and abnormal desquamation or exfoliation. Additional damage incurred as a result of both external and internal factors includes visible dead skin i.e., flaking, scaling, dryness, and roughness.

Currently, there are a number of personal care products that are available to consumers, which are directed toward improving the health and physical appearance of keratinous tissues such as the skin, hair, and nails. The majority of these products are directed to delaying, minimizing or even eliminating skin wrinkling, spots, and other histological changes typically associated with the aging of skin or environmental damage to human skin. Consumers prefer topically applied products since they are not only effective, but also safe and pleasant to use.

A variety of ingredients are used in such products to deliver the above benefits. It has been found by the present inventors that one of such ingredients, namely sucrose esters, may have difficulty to be dissolved in the product composition, especially when sucrose esters are contained at a higher level in the product composition and/or especially when sucrose esters are contained in an aqueous phase of the product composition. It has also been found that it may be preferred to dissolve sucrose esters in an aqueous phase of the product composition rather than oil phase, in view of providing fresh/light feel from the composition while providing benefits from the sucrose ester.

Based on the foregoing, there is a need for a method of manufacturing a cosmetic composition, which dissolves sucrose esters in cosmetic compositions, especially when the sucrose esters are contained at higher levels in the compositions and/or especially when the sucrose esters are contained in an aqueous phase of the cosmetic composition. There may also exist a need for a method of manufacturing a cosmetic composition, wherein the manufactured cosmetic compositions provide benefits from the sucrose ester while providing fresh/light feel from the composition.

SUMMARY OF THE INVENTION

The present invention is directed to a method of manufacturing a cosmetic composition comprising a step of preparing a mixture of:
(a) one or more esters of sucrose and fatty acids, wherein the fatty acids are selected from those having from about 12 to about 24 carbon atoms, and wherein the sucrose esters are selected from the group consisting of mono-ester, di-ester, tri-ester, tetra-ester, and mixtures thereof; and
(b) one or more solvents selected from those having Hildebrand Solubility Parameter of from about 23 to about $31.5 (J/cm^3)^{1/2}$ and Polar component of Hansen Solubility Parameter of from about 4.5 to about 10.5 $(J/cm^3)^{1/2}$.

It has now been surprisingly found that by the method of manufacturing the cosmetic composition of the present invention, the sucrose esters can be dissolved in the cosmetic compositions, even when the sucrose esters are contained at higher levels in the compositions and/or even when the sucrose esters are contained in an aqueous phase of the cosmetic composition.

Without being limited to the theory, it is believed that, by this method, the majority of the sucrose esters are contained in an aqueous phase of the compositions, when the compositions contain an aqueous carrier. Without being limited to the theory, it is believed that, such compositions provide sensorial feel that is light, non-greasy and/or fresh feel from the composition while providing benefits from the sucrose ester.

DETAILED DESCRIPTION OF THE INVENTION

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all ingredient percentages are based on the weight of the cosmetic composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive and combinable to form narrower ranges not explicitly disclosed. For example, delineated upper and lower range limits are interchangeable to create further ranges.

The compositions of the present invention can comprise, consist essentially of, or consist of, the essential components as well as optional ingredients described herein. As used herein, "consisting essentially of" means that the composition or component may only include additional ingredients that do not materially alter the basic and novel characteristics of the claimed composition or method. As used in the description and the appended claims, the singular forms "a", "an", and "the" are intended to include the plural forms as well, unless the context clearly indicates otherwise.

Definitions

"About" modifies a particular value by referring to a range equal to plus or minus twenty percent (+/−20%) or less (e.g., less than 15%, 10%, or even less than 5%) of the stated value.

"Apply" or "application", as used in reference to a composition, means to apply or spread the compositions of the present invention onto a human skin surface such as the epidermis.

"Derivative," herein, means amide, ether, ester, amino, carboxyl, acetyl, and/or alcohol derivatives of a given compound.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Cosmetic composition" means a composition comprising a cosmetic agent. Examples of cosmetic compositions include color cosmetics (e.g., foundations, lipsticks, concealers, and mascaras), skin care compositions (e.g., moisturizers and sunscreens), personal care compositions (e.g., rinse-off and leave on body washes and soaps), hair care compositions (e.g., shampoos and conditioners).

"Skin care" means regulating and/or improving a skin condition (e.g., skin health, appearance, or texture/feel). Some nonlimiting examples of improving a skin condition include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Synergy," and variations thereof, means that the effect provided by a combination of two or more materials is more than the additive effect expected for these materials.

"Treatment period," as used herein, means the length of time and/or frequency that a material or composition is applied to a target skin surface.

Method of Manufacturing

The method of manufacturing a cosmetic composition comprises the following step: Preparing a mixture of:

(a) one or more esters of sucrose and fatty acids, wherein the fatty acids are selected from those having from about 12 to about 24 carbon atoms, and wherein the sucrose esters are selected from the group consisting of mono-ester, di-ester, tri-ester, and tetra-ester, and mixtures thereof;

(b) one or more solvents selected from those having Hildebrand Solubility Parameter of from about 23 to about 31.5 $(J/cm^3)^{1/2}$ and Polar component of Hansen Solubility Parameter of from about 4.5 to about 10.5 $(J/cm^3)^{1/2}$.

The mixture comprises preferably from about 70% to about 100%, more preferably from about 80% to about 100%, still more preferably from about 90% to about 100%, by weight of the mixture, of the sum of the sucrose ester and the solvent, in view of solubilizing the sucrose esters.

In the mixture, the weight ratio between the sucrose ester and the solvent is preferably from about 1:1000 to about 1000:1, more preferably from about 1:100 to about 100:1, still more preferably from about 10:1 to about 1:10, even more preferably from about 5:1 to 1:5, further more preferably from about 2.5:1 to 1:2.5, in view of solubilizing the sucrose esters. In another embodiment, the weight ratio between the sucrose ester and the solvent is from about 2.5:1 to about 1:10, preferably from about 2.5:1 to about 1:5, in view of solubilizing the sucrose esters.

The method preferably further comprises the step of mixing the mixture and an aqueous carrier. The weight ratio between the aqueous carrier and the mixture is preferably from about 1000:1 to about 1:1000, more preferably from about 1:100 to about 100:1, still more preferably from about 1:10 to about 10:1, even more preferably from about 5:1 to about 1:5, further more preferably from about 2:1 to about 1:5. The addition of the aqueous carrier to the mixture may provide improved solubility of the sucrose ester. Too much aqueous carrier may cause reduced transparency/translucency and/or reduced solubility of the sucrose esters, and too less aqueous carrier may not see such improved solubility of the sucrose esters.

The above step of mixing the mixture and the aqueous carrier may comprises 2 sub-steps, i.e., first dilution and second dilution. The first dilution is a dilution of the mixture with the aqueous carrier. The second dilution is a dilution of the diluted mixture resulted from the $1^{st}$ dilution, to make the final product formulation of the cosmetic composition. In the second dilution, diluent can be anything which is included in the cosmetic composition, including but not-limited to the aqueous carrier. In the first dilution, the weight ratio between the aqueous carrier and the mixture is preferably from about 1:10 to about 10:1, more preferably from about 5:1 to about 1:5, further more preferably from about 2:1 to about 1:5. In the second dilution to make the final cosmetic composition, diluents and any other ingredients are added to q.s. to 100% of the cosmetic composition. In the second dilution, other ingredients, if included, such as thickeners, humectants, surfactants, pigments, powders, oils are concurrently and subsequently added.

Sucrose Esters

The sucrose esters useful herein are the esters of sucrose and fatty acids, wherein the fatty acids are selected from those having from about 12 to about 24 carbon atoms, preferably from about 12 to about 22 carbon atoms, more preferably from about 12 to about 18 carbon atoms, and wherein the sucrose esters are selected from the group consisting of mono-ester, di-ester, tri-ester, tetra-ester, and mixtures thereof. Preferably, the fatty acids are selected from those having saturated alkyl group having the above numbers of carbon atoms.

Preferably, the sucrose ester is included in the cosmetic composition at a level of from about 0.01% to about 50% preferably from about 0.1% to about 35%, more preferably from about 0.5% to about 25%, still more preferably from about 1% to about 20%.

Preferably, the sucrose ester useful herein contains from about 10% to about 100%, preferably from about 20% to about 100%, more preferably from about 50% to about 90% of higher esters selected from the group consisting of the di-ester, tri-ester, tetra-ester, and mixtures thereof.

In some instances, the sucrose ester may be a blend of two or more sucrose esters, wherein the two or more sucrose esters are present at a ratio of any one sucrose ester to another of 1:10 to 1:1 (e.g., 1:7, 1:5, 1:3, or 1:2). In some instances, the sucrose ester may be a blend of sucrose laurate and sucrose dilaurate, wherein sucrose laurate is present at 50% to 80%, by weight of the sucrose ester, and the sucrose dilaurate is present at 20% to 45%, by weight of the sucrose ester. Alternatively, the sucrose ester may be a blend of sucrose laurate, sucrose dilaurate and sucrose trilaurate, wherein the sucrose dilaurate is present at 35% or more, by weight of the sucrose ester. A particularly suitable example of a sucrose ester for use herein is Sucrose Dilaurate BC10034 available from BASF.

Solvent

The solvents useful herein are those selected from those having Hildebrand Solubility Parameter of from about 23 to about 31.5, preferably from about 23 to about 29 $(J/cm^3)^{1/2}$ and Polar component of Hansen Solubility Parameter of from about 4.5 to about 10.5. preferably from about 5 to about 9, more preferably from about 5.5 to about 8 $(J/cm^3)^{1/2}$, in view of solubilizing the sucrose esters.

One of the above solvents or a mixture of some of the above solvents can be used as long as each solvent meet the above parameters. Such solvents include, for example, following materials in below table:

| | Hildebrand Solubility Parameter $(J/cm^3)^{1/2}$ | Polar component of Hansen Solubility Parameter $(J/cm^3)^{1/2}$ |
|---|---|---|
| Ethanol | 26.52 | 8.8 |
| 1,2-Octandiol | 24.10 | 4.74 |
| 1,2-Hexanediol | 25.91 | 6.05 |
| Benzyl Alcohol | 23.79 | 6.3 |
| Hydrolyte-5 (Pentylene Glycol) | 27.21 | 7.01 |
| Phenoxyethanol | 24.13 | 6.7 |
| 1,3-Butandiol | 28.97 | 8.35 |
| Propylene Glycol | 31.47 | 10.31 |

Among them, highly preferred is pentylene glycol in view of a balance between improved solubility of sucrose ester and minimized possibility of skin irritation.

The solvent can be included in the cosmetic composition at a level from about 0.01% to about 90%, preferably from about 0.1% to about 50%, more preferably from about 0.5% to about 30%.

Followings are for reference purpose only, Hildebrand Solubility Parameter and Polar component of Hansen Solubility Parameter of ingredients which are often used in cosmetic compositions, but are not the solvent defined herein:

| | Hildebrand Solubility Parameter $(J/cm^3)^{1/2}$ | Polar component of Hansen Solubility Parameter $(J/cm^3)^{1/2}$ |
|---|---|---|
| Glycerin | 34.90 | 12.2 |
| Water | 47.80 | 42.3 |

Aqueous Carrier

Aqueous carrier useful herein are those excluding the solvent defined above. Preferably, the aqueous carrier is substantially water. Deionized water is preferably used. Water from natural sources including mineral cations can also be used, depending on the desired characteristic of the product.

In one embodiment, the aqueous carrier can be present at a level of from about 50% to about 99%, preferably from about 60% to about 98%, more preferably from about 70% to about 98%, still more preferably from about 80% to about 95%, by weight of the composition.

Cosmetic Composition

The cosmetic compositions herein are intended for topical application to human skin and contain the sucrose ester and solvent, and preferably further contain an aqueous carrier. The compositions herein may optionally include one or more additional skin actives or other ingredients of the type commonly included in topical cosmetic compositions.

The cosmetic compositions herein may be cosmetic compositions, pharmaceutical compositions, or cosmeceutical compositions, and may be provided in various product forms, including, but not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. In some instances, the composition form may follow from the particular dermatologically acceptable carrier chosen. For example, the composition (and carrier) may be provided in the form of an emulsion (e.g., water-in-oil, oil-in-water, or water-in-oil-in water) or an aqueous dispersion. Preferably, the cosmetic composition of the present invention is in the form of an oil-in-water emulsion, Dermatologically Acceptable Carrier The compositions disclosed herein may include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight.

The carrier can be in a wide variety of forms. In some instances, the solubility or dispersibility of the components (e.g., extracts, sunscreen active, additional components) may dictate the form and character of the carrier. Nonlimiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils).

Skin Conditioning Agent

Optionally, the composition of the present invention can further comprise a skin conditioning agent. These agents may be selected from humectants and emollients. The amount of skin-condition agent may range from about 1% to about 50%, preferably from about 2% to about 40%, more preferably from about 5% to about 30%, by weight of the composition.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin.

When the conditioning agent is an emollient it may be selected from hydrocarbons, fatty acids, fatty alcohols and esters.

Fatty Alcohol

The compositions herein may include a fatty alcohol. Fatty alcohols refer to high-molecular-weight, straight-chain primary alcohols that have the general structure:

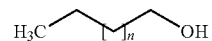

where n=8 to 32.

Fatty alcohols may be natural or synthetic, saturated or unsaturated, branched or straight-chain. Some nonlimiting examples of fatty alcohols commonly used in cosmetic compositions include caprylic, capryl, lauryl, myristyl, cetyl, stearyl, and behenyl alcohols. The fatty alcohols herein may be referred to generically by the number of carbon atoms in the molecule. For example, a "C12 alcohol" refers to an alcohol that has 12 carbon atoms in its chain (i.e., dodecanol).

The fatty alcohol may be included in the compositions herein at 0.0001% to 15% (e.g., 0.0002% to 10%, 0.001% to 15%, 0.025% to 10%, 0.05% to 7%, 0.05% to 5%, or even 0.1% to 3%) by weight of the composition.

Whitening Agents

The present compositions may contain a whitening agent. The whitening agent useful herein refers to active ingredients that not only alter the appearance of the skin, but further improve hyperpigmentation as compared to pre-treatment. Useful whitening agents useful herein include ascorbic acid compounds, vitamin B 3 compounds, azelaic acid, butyl hydroxy anisole, gallic acid and its derivatives, hydroquinoine, kojic acid, arbutin, mulberry extract, tetrahydrocurcumin, and mixtures thereof. Use of combinations of whitening agents is also believed to be advantageous in that they may provide whitening benefit through different mechanisms.

When used, the compositions preferably contain from about 0.1% to about 10%, more preferably from about 0.2% to about 5%, by weight of the composition, of a whitening agent.

Ascorbic acid compounds are useful whitening agents and ascorbyl glucoside is a preferred derivative of the ascorbic acid compounds.

Conditioning Agents

The compositions herein may include 0.1% to 50% by weight of a conditioning agent (e.g., 0.5% to 30%, 1% to 20%, or even 2% to 15%). Adding a conditioning agent can help provide the composition with desirable feel properties (e.g., a silky, lubricious feel upon application). Some non-limiting examples of conditioning agents include, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof. Particularly suitable examples of conditioning agents include volatile or non-volatile silicone fluids such as dimethicone copolyol, dimethylpolysiloxane, diethylpolysiloxane, mixed C1-30 alkyl polysiloxanes, phenyl dimethicone, dimethiconol, dimethicone, dimethiconol, silicone crosspolymers, and combinations thereof. Dimethicone may be especially suitable, since some consumers associate the feel properties provided by certain dimethicone fluids with good moisturization. Other examples of silicone fluids that may be suitable for use as conditioning agents are described in U.S. Pat. No. 5,011,681.

Thickening Agents

The compositions of the present invention, in some embodiments, may further include one or more thickening agents.

Nonlimiting classes of thickening agents include those selected from the following: carboxylic acid polymers, crosslinked polyacrylate polymers, polyacrylamide polymers, polysaccharides and gums.

When present, the composition preferably includes from about 0.01% to about 5%, more preferably from about 0.1% to about 4%, and still more preferably from about 0.1% to about 3%, by weight of the composition of the thickening agent.

Emulsifiers

When the composition is in the form of an emulsion, it may contain an emulsifier. Emulsifiers may be nonionic, anionic, cationic, or zwitterionic. Some non-limiting examples of emulsifiers are disclosed in U.S. Pat. Nos. 3,755,560, 4,421,769, U.S. Publication No. 2006/0275237 and McCutcheon's Detergents and Emulsifiers, North American Edition, pages 317-324 (1986). Suitable examples of emulsifiers include non-ionic emulsifiers such as Polysorbate 20, Polysorbate 80, Polygryceryl-4 caprate, and glycereth-25 pyrrolidonecarboxylic acid isostearate. A particularly suitable examples of an emulsifier for use in the compositions described herein is Polysorbate 20.

Other Optional Ingredients.

Compositions suitable for use in the method herein may include one or more optional ingredients known for use in topical cosmetic compositions, provided that the optional components do not unacceptably alter the desired benefits of the composition. In some instances, it may be desirable to select cosmetic actives that function via different biological pathways so that the actives do not interfere with one another. When the composition is in the form of an emulsion, the additional ingredients should not introduce instability into the emulsion (e.g., syneresis). For example, it may be desirable to select optional ingredients that do not form complexes with other ingredients in the composition, especially pH sensitive ingredients like vitamin B3 compounds, salicylates and peptides.

The additional ingredients should be suitable for use in contact with human skin tissue without undue toxicity, incompatibility, instability, allergic response, and the like. The optional components, when present, may be included at an amount of about 0.001% to 50% (e.g., 0.01% to 40%, 0.1% to 30%, 0.5% to 20%, or 1% to 10%), by weight of the composition. Some nonlimiting examples of additional ingredients include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunscreen agents, sunless tanning agents, lubricants, anti-acne agents, anti-cellulite agents, chelating agents, anti-wrinkle actives, anti-atrophy actives, phytosterols and/or plant hormones, N-acyl amino acid compounds, antimicrobials, and antifungals. Some particularly suitable examples of additional ingredient include one or more skin care actives selected from the group consisting of vitamin B3 compounds (e.g., niacinamide), n-acyl amino acids (e.g., undecylenoyl phenylalanine), vitamin E compounds (e.g., tocopheryl acetate), palmitoylated dipeptides (e.g., palmitoyl-lysine-threonine), palmitoylated pentapeptides (e.g., palmitoyl-lysine-threonine-threonine-lysine-serine), vitamin A compounds (e.g., retinol and retinyl propionate), and combinations thereof. Other non-limiting examples of optional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/0092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

Method of Use of the Cosmetic Composition

The method of use herein includes identifying a target portion of skin on a person in need of treatment and applying the composition to the target portion of skin over the course of a treatment period. The target portion of skin may be on a facial skin surface such as the forehead, perioral, chin, periorbital, nose, and/or cheek) or another part of the body (e.g., hands, arms, legs, back, chest). The person in need of treatment is one whose skin exhibits signs of oxidative stress, such as fine lines, wrinkles, hyperpigmentation, uneven skin tone, and/or other visible skin features typically associated with aging. In some instances, the target portion of skin may not exhibit a visible sign of skin aging, but a user (e.g., a relatively young user) may still wish to target such an area of skin, if it is one that typically develops such issues as a person ages. In this way, the present method may be used as a preventative measure to delay the onset of visible signs of skin aging.

The composition may be applied to a target portion of skin and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. The treatment period may last for at least 1 week (e.g., about 2 weeks, 4 weeks, 8 weeks, or even 12 weeks). In some instances, the treatment period will extend over multiple months (i.e., 3-12 months). In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a wrinkle or line) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied broadly to one or more skin surfaces. In certain embodiments, the compositions herein may be used as part of a multi-step beauty regimen, wherein the present composition may be applied before and/or after one or more other compositions.

Combinations

A. A method of manufacturing a cosmetic composition comprising a step of preparing a mixture of:
  (a) one or more esters of sucrose and fatty acids, wherein the fatty acids are selected from those having from about 12 to about 24 carbon atoms, preferably from about 12 to about 22 carbon atoms, more preferably from about 12 to about 18 carbon atoms, and wherein the sucrose esters are selected from the group consisting of mono-ester, di-ester, tri-ester, tetra-ester, and mixtures thereof;
(b) one or more solvents selected from those having Hildebrand Solubility Parameter of from about 23 to about 31.5, preferably from about 23 to about 29 $(J/cm^3)^{1/2}$ and Polar component of Hansen Solubility Parameter of from about 4.5 to about 10.5. preferably from about 5 to about 9, more preferably from about 5.5 to about 8 $(J/cm^3)^{1/2}$.

B. The method of the preceding feature, wherein the mixture comprises from about 70% to about 100%, preferably from about 80% to about 100%, more preferably from about 90% to about 100% of the sum of the sucrose ester and the solvent.

C. The method of any of the preceding features, wherein the fatty acids are selected from those having saturated alkyl group having from about 12 to about 24 carbon atoms.

D. The method of any of the preceding features, wherein the weight ratio between the sucrose ester and the solvent is from about 1:1000 to about 1000:1, preferably from about 1:100 to about 100:1, more preferably from about 10:1 to about 1:10, still more preferably from about 5:1 to 1:5, even more preferably from about 2.5:1 to 1:2.5.

E. The method of any of the preceding features, further comprising the step of mixing the mixture and an aqueous carrier.

F. The method of any of the preceding features, wherein the weight ratio between the aqueous carrier and the mixture is from about 1000:1 to about 1:1000, preferably from about 1:100 to about 100:1, more preferably from about 1:10 to about 10:1, still more preferably from about 5:1 to about 1:5, even more preferably from about 2:1 to about 1:5.

G. The method of any of the preceding features, wherein the step of mixing the mixture and an aqueous carrier comprises first dilution step and second dilution step, wherein in the first dilution step, the weight ratio between the aqueous carrier and the mixture is from about 1:10 to about 10:1, preferably from about 5:1 to about 1:5, more preferably from about 2:1 to about 1:5.

H. The method of any of the preceding features, wherein the sucrose ester contains from about 10% to about 100%, preferably from about 20% to about 100%, more preferably from about 50% to about 90% of higher esters selected from the group consisting of the di-ester, tri-ester, tetra-ester, and mixtures thereof.

I. The method of any of the preceding features, wherein the cosmetic composition comprises from about 0.01% to about 50% preferably from about 0.1% to about 35%, more preferably from about 0.5% to about 25%, still more preferably from about 1% to about 20% of the sucrose ester.

EXAMPLES

TABLE 1

Mixture (percent by weight)

| | Mixture Ex. 1 | Mixture Ex. 2 | Mixture Ex. 3 | Mixture Ex. 4 | Mixture Ex. 5 | Mixture CEx. i (Comparative example) |
|---|---|---|---|---|---|---|
| Sucrose ester (Sucrose Dilaurate BC10034 available from BASF) | 33.3% | 20% | 33.3% | 20% | 20.0% | 33.3% |
| Pentylene Glycol | 66.7% | 80% | | | 40% | |
| Ethanol | | | 66.7% | | | |
| Benzyl Alcohol | | | | 80% | 40% | |
| Glycerin | | | | | | 66.7% |
| Solubilization of the sucrose ester ** i | Completely solubilized (clear solution) | Completely solubilized (clear solution) | Completely solubilized (clear solution) | Completely solubilized (clear solution) | Completely solubilized (clear solution) | Bulk of solid sucrose esters is observed (opaque, non-homogeneous solution) |

** i) Visual observation after 24 hours after mixing at 80° C. for 60 min.

TABLE 2

First dilution (percent by weight)

| | First Dilution Ex. 1 | First Dilution Ex. 2 | First Dilution Ex. 3 | First Dilution Ex. 4 | First Dilution Ex. 5 | First Dilution CEx. i (Comparative example) |
|---|---|---|---|---|---|---|
| Mixture from Table 1 | 50% of Mixture Ex. 1 | 60% of Mixture Ex. 2 | 50% of Mixture Ex. 3 | 70% of Mixture Ex. 4 | 50% of Mixture Ex. 5 | 50% of Mixture CEx. i |
| Deionized water | 50% | 40% | 50% | 30% | 50% | 50% |
| Solubilization of the sucrose ester ** ii | Completely solubilized (clear | Completely solubilized (clear | Completely solubilized (clear | Completely solubilized (clear | Completely solubilized (clear | Bulk of solid sucrose esters is observed |

TABLE 2-continued

First dilution (percent by weight)

|  | First Dilution Ex. 1 | First Dilution Ex. 2 | First Dilution Ex. 3 | First Dilution Ex. 4 | First Dilution Ex. 5 | First Dilution CEx. i (Comparative example) |
|---|---|---|---|---|---|---|
|  | solution) | solution) | solution) | solution) | solution) | (opaque, non-homogeneous solution) |

** ii) Visual observation after mixing the mixture and deionized water at room temperature for 1 min.

TABLE 3

Second dilution (percent by weight)

| | | Second Dilution Ex. 1 | Second Dilution Ex. 2 | Second Dilution Ex. 3 | Second Dilution Ex. 4 | Second Dilution Ex. 5 | Second Dilution CEx. i (Comparative example) |
|---|---|---|---|---|---|---|---|
| First dilution from Table 2 | | 6% of First Dilution Ex. 1 | 10% of First Dilution Ex.2 | 0.1% of First Dilution Ex. 3 | 1% of First Dilution Ex. 4 | 6% of First Dilution Ex. 5 | 6% of First Dilution CEx. i |
| Oil phase ingredients | Triethylhexanoin | 3.5% | 2.0% | | 3.0% | 0.5% | 3.5% |
| | Eldew PS-203 *4 | 1.5% | 1.0% | | | 0.25% | 1.5% |
| | Dimethicone 5cst | | | 1.75% | | 2.0% | |
| Water phase ingredients | PEG32 | 1% | | | 2% | | 1% |
| | Glycerin | 4% | 3% | 5.5% | | 5% | 4% |
| | Xylitol | 0.5% | | 1.0% | | | |
| | Niacinamide | 5% | 5% | 2% | 5% | 5% | 5% |
| | Polysorbate 20 | 0.25% | | 0.25% | | 0.25% | 0.25% |
| | Sepigel 305 *1 | 0.6% | 0.6% | | 1.0% | 2.0% | 0.6% |
| | Ultrez 20 *2 | 0.25% | 0.25% | | 1.0% | | 0.25% |
| | Sepimax Zen *3 | | | 2.4% | | | |
| | Aminomethyl Propanol | 0.15% | 0.15% | | 0.6% | | 0.15% |
| | Deionized water | q.s. to 100% | q.s. to 100% | q.s. to 100% | q.s. to 100% | q.s. to 100% | q.s. to 100% |
| Solubilization of the sucrose ester ** iii | | Completely solubilized (homogeneous composition) | Completely solubilized (homogeneous composition) | Completely solubilized (homogeneous composition) | Completely solubilized (homogeneous composition) | Completely solubilized (homogeneous composition) | Solid sucrose esters are observed (non-homogeneous composition) |

Ingredients
*1          Sepigel 305:         Containing 40% of Polyacrylamide as active.
                                  INCI: Polyacrylamide & Water & C13-14 Isoparaffin & Laureth-7
*2          Ultrez 20:           INCI: Acrylates/C10-30 Alkyl Acrylate Crosspolymer
*3          Sepimax Zen:         INCI: Polyacrylate crosspolymer-6
*4          Eldew PS-203         INCI: Phytosteryl/Octyldodecyl Lauroyl Glutamate
** iii) Visual observation after mixing as follows:
(a) Water phase ingredients are mixed at room temperature until being homogenized;
(b) Such homogenized water phase ingredients from (a) and the First dilution from table 2 are mixed for 5 min; and
(c) Such mixed ingredients from (b) and oil phase ingredients are mixed by a homomixer at 5000 rpm at room temperature for 5 min.

Second Dilutions Ex. 1 through Ex. 5 are skin care compositions made by the method of manufacturing of the present invention. Second Dilution CEx. i is a skin care composition made by a different method of manufacturing from the present invention, and provided as a comparative example. As shown in the above tables, the method of the present invention can dissolve sucrose esters in skin care compositions, while the comparative example can not dissolve sucrose esters.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a cosmetic composition comprising an aqueous continuous phase and a dispersed oil phase comprising:
   a. preparing a mixture consisting of:
      i. a sucrose ester comprising a fatty acid portion comprising from about 12 to about 24 carbon atoms, and wherein the sucrose ester comprises from about 10% to about 100%, by weight of the sucrose ester, of a higher ester selected from the group consisting of di-ester, tri-ester, tetra-ester, and mixtures thereof; and
      ii. a solvent selected from those having a Hildebrand Solubility Parameter of from about 23 to about $31.5(J/cm^3)^{1/2}$ and a Polar component of Hansen Solubility Parameter of from about 4.5 to about 10.5 $(J/cm^3)^{1/2}$;
   b. dilution of the mixture with a first aqueous carrier to form a first dilution comprising a weight ratio between the first aqueous carrier and the mixture of from about 1:10 to about 10:1;
   c. dilution of the first dilution with a second aqueous carrier to form the aqueous continuous phase of the cosmetic composition; wherein a majority of the sucrose esters are dissolved in the aqueous continuous phase;
   d. mixing the oil phase into the continuous phase to form the cosmetic composition; wherein the cosmetic composition comprises from about 50% to about 99% of the first and second aqueous carriers; wherein the composition is a moisturizer.

2. The method of claim 1, wherein the solvent has Hildebrand Solubility Parameter of from about 23 to about 29 $(J/cm^3)^{1/2}$ and the Polar component of Hansen Solubility Parameter of from about 5 to about $9(J/cm^3)^{1/2}$.

3. The method of claim 1, wherein the solvent has the Polar component of Hansen Solubility Parameter of from about 5.5 to about 8 $(J/cm^3)^{1/2}$.

4. The method of claim 1, wherein the weight ratio between the sucrose ester and the solvent is from about 1:100 to about 100:1.

5. The method of claim 4, wherein the weight ratio between the sucrose ester and the solvent is from about 5:1 to 1:5.

6. The method of claim 1, wherein the weight ratio between the first aqueous carrier and the mixture is from about 5:1 to about 1:5.

7. The method of claim 6, wherein the weight ratio between the first aqueous carrier and the mixture is from about 2:1 to about 1:5.

8. The method of claim 1, wherein the sucrose ester contains from about 20% to about 100%, by weight of the sucrose ester, of higher esters selected from the group consisting of the di-ester, tri-ester, tetra-ester, and mixtures thereof.

9. The method of claim 8, wherein the sucrose ester contains from about 50% to about 90%, by weight of the sucrose ester, of higher esters selected from the group consisting of the di-ester, tri-ester, tetra-ester, and mixtures thereof.

10. The method of claim 1, wherein the cosmetic composition comprises from about 0.1% to about 35%, by weight of the cosmetic composition, of the sucrose ester.

11. The method of claim 10, wherein the cosmetic composition comprises from about 1% to about 20%, by weight of the cosmetic composition, of the sucrose ester.

12. The method of claim 1, wherein the solvent is pentylene glycol.

13. The method of claim 1, wherein the first and/or second aqueous carriers comprise water and one or more of the following ingredients: glycerin, xylitol, and/or niacinamide.

14. The method of claim 1, wherein the oil phase comprises dimethicone.

15. The method of claim 1, wherein the sucrose ester is a blend of sucrose laurate and sucrose dilaurate.

* * * * *